United States Patent [19]

Mikitenko et al.

[11] 4,168,209

[45] Sep. 18, 1979

[54] PROCESS FOR PURIFYING BENZENE AND TOLUENE BY EXTRACTIVE AZEOTROPIC DISTILLATION

[75] Inventors: Paul Mikitenko, Chatou; Lionel Asselineau, Paris, both of France

[73] Assignee: Institut Francais du Petrole, Rueil-Malmaison, France

[21] Appl. No.: 884,512

[22] Filed: Mar. 8, 1978

[30] Foreign Application Priority Data

Mar. 8, 1977 [FR] France ................................ 77 07242

[51] Int. Cl.² .......................... B01D 3/36; C07C 7/06; C07C 7/08
[52] U.S. Cl. ......................................... 203/2; 203/53; 203/60; 203/84; 203/85; 585/834; 585/862
[58] Field of Search ....................... 203/53, 54, 60, 55, 203/96, 97, 92, 93, 84, 85, 2; 260/674 R, 674 A

[56] References Cited

U.S. PATENT DOCUMENTS

| | | | |
|---|---|---|---|
| 2,022,809 | 12/1935 | Kramer .................................... | 203/2 |
| 2,684,326 | 7/1954 | Boyd ....................................... | 203/2 |
| 2,742,411 | 4/1956 | Leary et al. ............................ | 203/46 |
| 3,884,769 | 5/1975 | Mikitenko et al. ..................... | 203/53 |

*Primary Examiner*—Wilbur L. Bascomb, Jr.
*Attorney, Agent, or Firm*—Millen & White

[57] ABSTRACT

Process for separating benzene and/or toluene from mixtures thereof with saturated hydrocarbons, by extractive distillation using an aliphatic N-alkylamide as extraction solvent, comprising introducing in the distillation column, above the level of introduction of the extraction solvent, liquid water in an amount and under such conditions that said water is completely vaporized without substantially diluting the solvent, condensing the vapors discharged from the top of the column and dividing the resulting condensate into a phase of liquid saturated hydrocarbons, and a phase of water.

15 Claims, 2 Drawing Figures

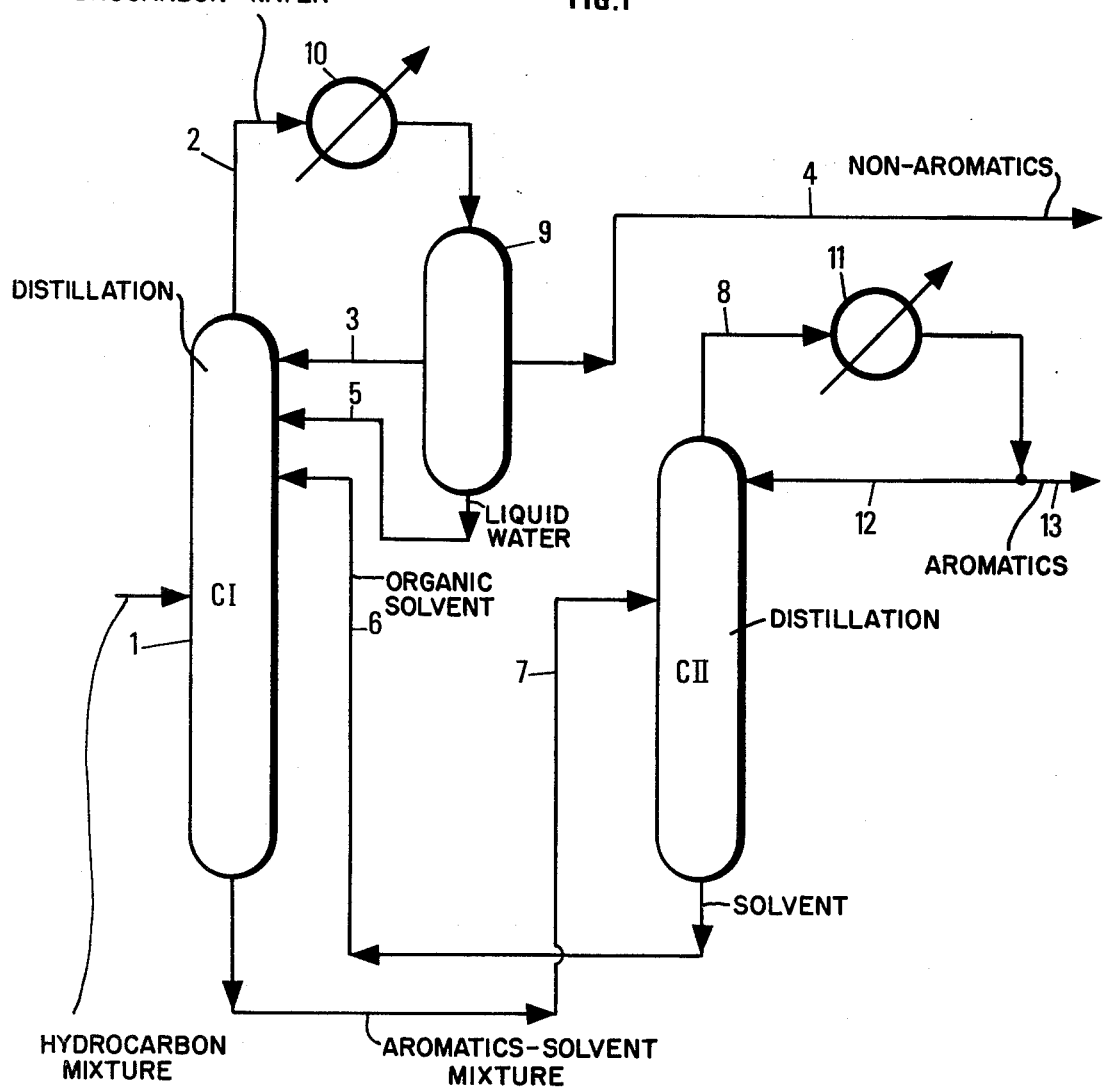

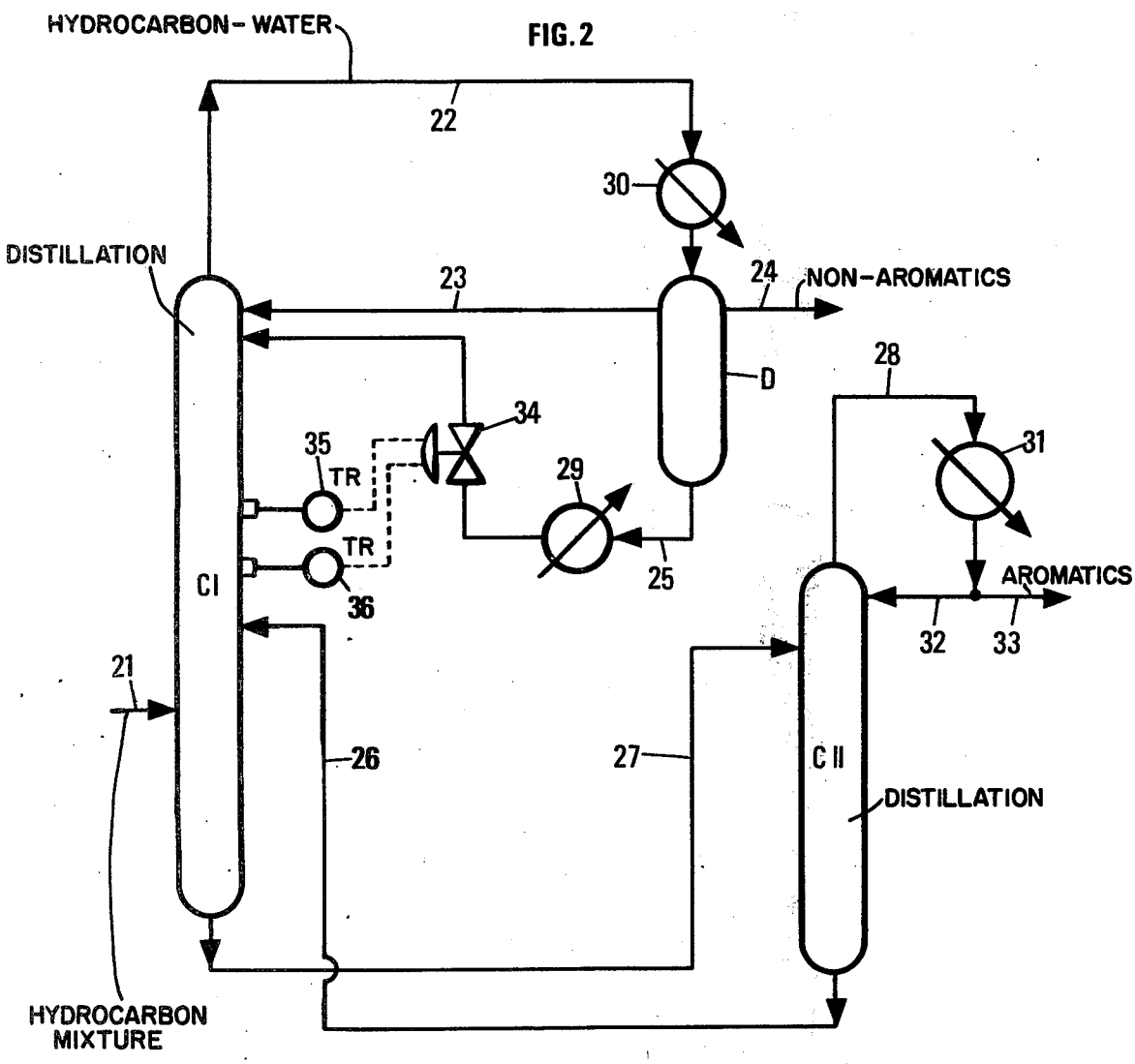

PROCESS FOR PURIFYING BENZENE AND TOLUENE BY EXTRACTIVE AZEOTROPIC DISTILLATION

This invention concerns a process for purifying benzene and toluene by extractive distillation.

The extractive distillation of aromatic hydrocarbons is a well known operation. Many solvents have been proposed. The use of alkylamides is proposed in particular in U.S. Pat. Nos. 3,114,783 and 3,884,769. However, the latter patent specification states that some difficulties are encountered as the result of the use of alkylamides: these solvents form azeotropes with saturated hydrocarbons having 6, 7 and 8 carbon atoms, so that a non negligible amount of solvent is carried away with the effluent from the top of the extractive distillation column, requiring a further purification step. The U.S. Pat. No. 3,884,769 makes the proposal to meet with this disadvantage by injecting steam into the top effluent of the distillation column. The resulting improvement is substantial: the carrying away of the solvent with the top hydrocarbon fraction is substantially reduced. The condensed water may be vaporized and reinjected into the column.

It is also known to inject water into an extractive distillation column so as to admix the same with the extraction solvent (British Pat. No. 1,428,228). Such a technique is not applicable to alkylamides which tend to hydrolyze in contact with water in the hot portions of the extractive distillation unit.

It has now been shown that the process according to U.S. Pat. No. 3,884,769 may be still improved by injecting water in the liquid form instead of steam. By this way it is possible not only to avoid use of a vaporizer and to save energy, but also it has been observed surprisingly that, with an equal amount of water, the aromatic hydrocarbons are of higher purity than in the case of injection of steam, in other words, the same purity of the aromatic hydrocarbons produced by the process can be obtained at a much smaller rate of water injection and/or with a lower recycling rate of the saturated hydrocarbons to the column, whereby a significant energy saving is achieved together with the possibility to reduce the size of the plant.

It is only by water injection, with use of a solvent which does not result in the formation of an azeotrope with water, and provided with the mixture of water with the solvent is avoided, that it is possible to obtain the advantages of the present process. As a matter of fact, in the case of water injection in a column operated with a solvent forming such an azeotrope, e.g. furfural, according to a known technique (U.S. Pat. No. 2,742,411) it is not possible to recover the solvent carried along with the distillate except by proceeding to complementary operations of washing, stripping and distillation which are complicated and costly. Similarly, when water is admixed to a large extent with the extraction solvent in the column, there is observed a noticeable decomposition of the alkylamides by hydrolysis in the hot portions of the column.

This invention concerns a process for separating benzene and/or toluene from mixtures containing the same, together with at least one paraffinic or cyclic saturated hydrocarbon, by extractive distillation, in a distillation zone, in the presence of an extraction solvent consisting essentially of an aliphatic N-alkylamide, characterized in that, in order to reduce the solvent losses by entrainment with the distillate, liquid water is introduced in the portion of the distillation zone located between the injection point of the extraction solvent and the top of the distillation column, in an amount and under such conditions that said water vaporizes completely in said portion of the distillation zone without substantially diluting the solvent, and in that the vapors discharged at the top are condensed and the condensate is separated into two liquid phases, a first liquid phase containing essentially saturated hydrocarbons and a second liquid phase containing essentially condensed water vapor.

According to a preferred embodiment, at least a portion of the second liquid phase is recycled directly to the distillation zone, to form at least a portion of the liquid water introduced in said distillation zone.

As the alkylamide, there is preferably used N,N-dimethylformamide and/or N,N-dimethylacetamide.

Water is introduced in the liquid form in an amount and under such conditions that it is completely vaporized in the distillation column so as to be carried along with the hydrocarbon vapors evolving from the top of the column, without flowing to a substantial extent down to the injection point of the extraction solvent.

It has been observed that when the distillation unit is further heated, for example by means of a reboiler, and water is introduced in the liquid form, the latter is vaporized by thermal exchange on a few plates of the column by contact with the ascending vapors. The amount of additional heat so supplied depends essentially on the amount of injected water which is adapted to each hydrocarbon mixture to be treated and to the desired specifications for the products.

According to an embodiment of the process, the hydrocarbon mixture to be separated is introduced into a distillation zone at an intermediary point thereof; the extraction solvent is introduced at a point of the distillation zone above the point of introduction of the hydrocarbon mixture and water is introduced, in the liquid form, at a point of the distillation zone above the point of introduction of the extraction solvent, under such conditions that said water cannot dilute the solvent; the top product from the distillation zone is condensed; the obtained condensate is separated into two liquid phases, a first phase containing non-aromatic hydrocarbons and a second phase containing water; said first and second phases are withdrawn separately, the product from the bottom of said distillation zone, containing aromatic hydrocarbons and the extraction solvent is discharged and the solvent is separated, in a known manner, from the aromatic hydrocarbons, to obtain on the one hand, the recovered extraction solvent and, on the other hand, the aromatic hydrocarbons.

There is advantageously used 5 to 50%, preferably 10 to 35% by weight of water with respect to the non-aromatic hydrocarbons of the charge. The ratio by volume of the solvent to the hydrocarbon charge is, for example, from 0.4 to 15, preferably from 1 to 6.

Although this is not obligatory according to the invention, it is however preferred to provide a few plates, i.e. for example 1 to 5 plates, or packing, for example Raschig rings, at the upper portion of the distillation column, between the points of injection of liquid water and of the extraction solvent, in order to ensure the thermal exchange which produces the water vaporization.

The distillation conditions are otherwise conventional: particularly, it is advantageous to increase the efficiency of the operation by feeding back to the column, as reflux, a portion of the first condensed phase, the other portion being merely withdrawn.

The recovered extraction solvent, after its separation from the aromatics, is advantageously recycled to the column.

For separating the aromatic hydrocarbons from the extraction solvent, it is possible to proceed by distillation or by liquid-liquid re-extraction of the aromatics by means of a third solvent such as a liquid paraffinic hydrocarbon which may be subsequently separated from said aromatic hydrocarbons by distillation, this being the case, for example, of liquid butane, pentane or heavy cuts such as gas oil or kerosene. The resulting aromatic hydrocarbons have a high degree of purity.

FIG. 1 illustrates a preferred embodiment of the invention.

The hydrocarbon mixture containing benzene and/or toluene to be extracted, is fed to column CI, preferably at a temperature close to its bubble point, through line 1. The organic solvent is introduced into said column through line 6 which opens into the column at a level thereof above that of introduction of the initial hydrocarbon mixture, at a temperature close to that prevailing in the column at the same level for the determined operating conditions. The ratio by volume of the solvent to the hydrocarbon charge is advantageously from 0.4 to 15 and, preferable, from 1 to 6. The organic solvent, which is the less volatile compound, flows mainly, in the liquid form, towards the bottom of column CI, while carrying along therewith the aromatic hydrocarbons and modifying their volatility with respect to the paraffinic or naphthenic impurities which were initially present therewith. The aromatics-solvent mixture is discharged from column CI through line 7 and fed to column CII, where, by means of a conventional distillation, it is separated into aromatics which are withdrawn from the top, through line 8, condenser 11 and line 13, and regenerated solvent, at the bottom, which is recycled to column CI through line 6. A portion of the aromatic hydrocarbons may be fed back to column CII through line 12. According to an alternative embodiment of the process, and in the case of simultaneous purification of benzene and toluene, the effluent from the bottom of column CI, comprising the organic solvent and the aromatics, is fed to a column CII, wherefrom purified benzene is withdrawn at the top and the organic solvent, containing toluene, at the bottom. The latter mixture is fed to a column CIII, not shown, which provides at the top purified toluene and, at the bottom, the organic solvent which is recycled to column CI through line 6.

Above the point of introduction of the organic solvent, there is injected liquid water (line 5), at a temperature generally between room temperature and the boiling temperature of water under the pressure conditions prevailing in the column. There is advantageously used 5 to 50%, preferably 10 to 35% by weight of water with respect to the non-aromatic hydrocarbons of the treated charge.

Water forms with the present hydrocarbons, i.e. mainly nonaromatic hydrocarbons, an azeotropic system which is more volatile with respect to the organic solvent than the hydrocarbons alone, which distills at the top of the column and is discharged through line 2. This effluent is condensed in unit 10 and settled into two liquid phases in a decanter 9. A portion of the upper phase, consisting of hydrocarbons, is fed up, through line 3, to column CI, as reflux while the other portion is withdrawn from the unit through line 4. The lower phase consisting essentially of water, may be either discharged from the unit, or preferably recycled to column CI through line 5, under the above defined conditions.

The invention proposes a mode of adjustment of the water injection, which can be operated automatically. This adjustment consists fundamentally of the regulation of the water flow in relation with the temperature prevailing at a point below the point of water injection and above the point of solvent injection.

The temperature is measured, for example, on the fourth plate (or on a plate at a higher level) above the plate receiving the solvent (or the higher plate receiving the solvent, when the latter is introduced at several points); under these conditions, for sake of security, at least three plates separate the point of solvent injection from the point of temperature measurement.

When the temperature decreases at the measuring point, the water flow is reduced or stopped; when the temperature increases, the flow rate is increased. It has been observed that this regulation is relatively easy since the temperature variations may be substantial; they may reach or even exceed 10° C., according to the nature of the hydrocarbons. These temperature variations are due to the presence or the absence of water-hydrocarbon azeotropic mixture at the measuring point level. As a matter of fact, when water flows down to the measuring point, it forms with the hydrocarbons a heteroazeotropic system whose boiling point is substantially lower than that of the one or more hydrocarbons when present alone at this level. The reduction of the water injection results in the rising, in the column, of the point of formation of the heteroazeotropic mixture and the temperature of the measuring point increases. Thus, it is possible to select at will the level of formation of the azeotropic mixture.

According to an improvement to this process, the temperature is measured at two separate points of two different levels in the above-defined zone, i.e. between the respective injection points of water and solvent: a temperature decrease at the lower measuring point controls the reduction or the closure of the water supply; the reopening of the water supply or the increase of the flow rate are controlled by a temperature increase at the upper measuring point. The spacing between the two measuring points may vary in a wide range; it is at the minimum the space of a plate, but it is preferred to use a space of 2 to 10 plates.

The process is preferably conducted as follows: the mixture of hydrocarbons to be separated, containing at least one aromatic hydrocarbon and at least one saturated hydrocarbon, is introduced into a distillation zone, at an intermediary point thereof; the extraction solvent is introduced at a point of the distillation zone above the point of introduction of the hydrocarbons mixture, and water is introduced at a point of the distillation zone above the point of introduction of the extraction solvent, the top product of the distillation zone or distillate is condensed, the resulting condensate is separated into two liquid phases, a first phase consisting essentially of saturated hydrocarbon and a second phase essentially of water. From the bottom of the distillation zone is discharged the bottom product containing the aromatic hydrocarbon and the extraction solvent, and the solvent is separated from the aromatic hydrocarbon, in a known manner, to obtain, on the one hand, the recovered extraction solvent and, on the other hand, the aromatic hydrocarbon.

It must be understood that this definition includes the treatment of several mainly saturated and/or aromatic hydrocarbons in admixture; said mixture may optionally contain small amounts of monoolefins (preferably less than 5% by volume).

According to a preferred embodiment, the efficiency of the fractionation is increased by feeding back to the distillation column, as reflux, a portion of the first condensed phase. The point of introduction of said reflux is preferably above the point of introduction of water.

It is also advantageous to feed back to the column, the condensed aqueous phase, either as such or after heating or even vaporization, so as to provide the necessary water. Finally, the recovered extraction solvent is advantageously recycled to the column.

The aromatic hydrocarbons can be separated from the extraction solvent by distillation or by liquid-liquid re-extraction of the aromatics by means of a third solvent such as a liquid paraffinic hydrocarbon, subsequently separable by distillation from said aromatic hydrocarbons, such as, for example, liquid butane, pentane or heavy cuts such as gas-oil or kerosene.

It is essential, according to the invention, to inject water into the distillation column as above mentioned. As a matter of fact, if water was injected on the path of the vapors issued from the extractive distillation column, at the inlet of the condenser, the entrainment of the extraction solvent vapors could not be avoided: after passage through the condenser, two phases would be obtained, one aqueous phase and one hydrocarbon phase which would contain substantial amounts of said solvent.

FIG. 2 illustrates a preferred mode of operation of the invention.

The hydrocarbon mixture containing benzene and/or toluene to be extracted is fed, preferably at a temperature close to its bubble point, to column CI, through line 21. The organic solvent is introduced in said column through line 26, opening in that column at a level obligatorily higher than that of introduction of the initial hydrocarbon mixture, at a temperature close to that prevailing in the column at the same level. The ratio by volume solvent/hydrocarbon charge is advantageously from 0.4 to 15 and, preferably, from 1 to 6. The organic solvent, which is the less volatile compound, flows down, in the liquid form, to the bottom of column CI, carrying therewith the aromatics.

The solvent-aromatics mixture is discharged from column CI through line 27 and fed to column CII where, by conventional distillation, aromatics are separated at the top through line 28, condenser 31 and line 33, and the regenerated solvent, withdrawn from the bottom, is recycled to column CI through line 26. A portion of the aromatics is fed to column CII through line 32. According to an alternative embodiment of the process, and in the case of a simultaneous purification of benzene and toluene, the effluent from the bottom of column CI, comprising the organic solvent and the aromatics, is fed to column CII, wherefrom purified benzene is withdrawn at the top and the organic solvent, containing toluene, at the bottom. The latter mixture is fed to a column CIII, not shown, providing, at the top, purified toluene and, at the bottom, the organic solvent which is recycled to column CI through line 26.

Through line 25, there is injected water which passes optionally through exchanger 29 when it is desired to heat or even to vaporize it. There is used advantageously 5 to 50%, preferably 10 to 35% by weight of water with respect to the non-aromatic hydrocarbons of the treated charge. The amount of water depends on the more or less large opening of the valve 34 controlled by either the temperature recorder 36 alone or both temperature recorders 35 and 36.

Water forms with the present hydrocarbons, i.e. mainly the non-aromatic ones, an azeotropic system more volatile with respect to the organic solvent than the hydrocarbons alone, which distills at the top of the column and is discharged through line 22. This effluent is condensed in unit 30 and settled into two liquid phases in decanter D. A portion of the upper phase, consisting of hydrocarbons, is fed back, through line 23, to column CI, as reflux, while the other portion is discharged from the unit through line 24. The lower phase, consisting essentially of water, may be either withdrawn from the unit or recycled to column CI, through line 25, under the above defined conditions.

The operation is as above described. When the recorder 36 is alone, a temperature decrease controls the relative or complete closure of valve 34; on the contrary, a temperature increase controls the re-opening of the valve. When both recorders are used, the recorder 36 (in case of temperature decrease) controls the relative or total closure of valve 34 and the recorder 35 (in case of temperature increase) controls the opening of valve 34.

Modifications may be brought to the device without departing from the scope of the invention. In particular, it is possible to make use of secondary monitorings, for example the water flow rate may be made dependent, to a certain extent, on the composition and/or flow rate of the hydrocarbon charge, on the heating of the column bottom may be controlled by the temperature measured at a point of the column selected at will. All these controls are well known and need not to be described here.

While proceeding according to the invention, it has been made apparent that almost the entirety of the organic solvent is found at the bottom of the column with the aromatics and that the non-aromatic hydrocarbons discharged at the top of the column are practically free of organic solvent, this being not the case when proceeding to a conventional extractive distillation by using the same organic solvent without water injection.

It was also apparent that the organic solvent alone is found at the column bottom with the purified aromatic hydrocarbons, without injected water, which is withdrawn essentially at the top of the column.

These essential characteristics confer to the process of the invention several advantages as compared with the conventional extractive distillation by means of solvents whose boiling temperature is relatively close to that of the hydrocarbons they permit to separate.

A first advantage, already mentioned, is that it makes possible to avoid any loss of extraction solvent at the top of the distillation column.

A second advantage is that the optimum water flow rate to inject for avoiding solvent losses is automatically delivered through a regulator for defined running conditions (composition of the charge, solvent rate, yield of aromatics).

Another advantage is that the optimum water flow rate is adjustable by means of the regulator when the operating conditions vary.

Still another advantage results from the fact that the extraction solvent is not shared between the top and the bottom of the separation column: all the solvent is used for the purification of the aromatics and, consequently, at equal purity of aromatics, the amount of solvent to be introduced into the column is lower.

Another advantage is that water and the extraction solvent are never in direct contact with each other in the liquid phase, in the hot portions of the apparatus. There is thus avoided possible chemical reactions between the two solvents. It is known, for example, that the dialkylamides may be slightly hydrolyzed in the presence of water, in the liquid phase, at a temperature higher than 120° C. Such a reaction is avoided in the present case.

Examples 1 and 2 make possible a quantitative comparison between the two modes of operation of the process which differ only by the physical state of the injected water (example 1: steam, example 2: liquid). It is remarkable that, in both cases, water does not flow down to the point of introduction of the solvent and the latter has always a water content smaller than 0.1% (by weight).

The amount of liquid water to be injected, and its injection point as well as the amount of the organic reflux are, for a given charge, dependent on the specifications of the desired products.

Example 3 illustrates an embodiment where dimethylformamide is removed from the non-aromatic hydrocarbons, and non-aromatics from benzene to a lesser extent. In that case, liquid water is introduced at the same point as the organic reflux whose flow rate amounts to only about 4% of that used in the operating conditions illustrated in examples 1 and 2; consequently, the liquid flow rate has been reduced and does not amount to more than about one third of that used in the preceding cases.

Example 4 shows that when all the operation parameters of example 3 are maintained, but water is injected in the form of steam as in example 1, the removal of dimethylformamide in the non-aromatic distillate as well as the degree of purification of the produced benzene are not as good.

Example 5 illustrates the operation of the automatic regulation device for water injection.

EXAMPLE 1 (comparative example)

In a distillation column of the Oldershaw type having a 2.5 cm inner diameter, provided with 65 perforated plates with overflow, there are injected respectively on the 25$^{th}$, 50$^{th}$, 60$^{th}$ plates from the bottom of the column:

A benzenic cut whose composition is given in Table 1, at a rate of 204 g/h and at a temperature of 70° C.

Dimethylformamide at a rate of 646 g/h and at a temperature of 60° C.

Vaporized water at a rate of 15.5 g/h and at a temperature of 120° C.

The column is maintained under steady state conditions by regulating the heating of the boiler. The total amount of water escapes from the top without diluting the dimethylformamide.

The distillate recovered at the top at a temperature of 69° C. is condensed and settled into two phases: a lower aqueous phase which is recycled to the column, after vaporization, to the precedingly defined level, and an upper organic phase, whose composition is indicated in Table I, consisting essentially of non-aromatic impurities of the benzenic cut, a portion of which i.e. 72.5 cc/h is withdrawn and discharged from the system and the other portion, i.e. 174 cc/h is fed back to the top of the column, as reflux.

From the bottom of the column, where the temperature is 120° C., there is withdrawn a mixture consisting essentially of dimethylformamide and benzene, which is fed back at a rate of 799 g/h to the middle of a second column, of the Oldershaw type, having a 2.5 cm inner diameter and provided with 40 perforated plates with overflow. From the top of the column there is withdrawn purified benzene (Table I, column 5), ⅔ of which are fed back as reflux; from the bottom of the said column is withdrawn dimethylformamide free of benzene, which is recycled, at a rate of 646 g/h, to the first column after being cooled down to 60° C.

TABLE I

| Constituent | (% by weight) | | | Produced Benzene | |
|---|---|---|---|---|---|
| | Solvent | Charge | Distillate | Ex. 1 | Ex. 2 |
| Hexane | — | 8.41 | 33.5 | <0.0010 | <0.0010 |
| Cyclohexane | — | 12.9 | 51.6 | 0.0064 | 0.0020 |
| Heptane | — | 3.45 | 13.7 | 0.0127 | 0.0050 |
| Methylcyclohexane | — | 0.13 | 0.45 | 0.0098 | 0.0072 |
| Benzene | <0.1 | 75.1 | 0.66 | >99.9 | >99.9 |
| Water | <0.1 | <0.05 | <0.05 | <0.05 | <0.05 |
| Dimethylformamide | >99.8 | — | 0.0015 | <0.001 | <0.001 |

EXAMPLE 2

The distillation is conducted under similar conditions to those described in example 1, with the same recycle rates, the same charge, the same solvent, but water is no longer vaporized outside the column; it is introduced, in the light state, at a temperature of 60° C. The total amount of said water is vaporized without diluting the solvent.

No noticeable difference appears in the temperatures which prevail in each of the two columns as compared to those mentioned in example 1.

The composition of the non-aromatic distillate, within experimental error, is also similar to that obtained precedingly and reported in Table I, colomun 4.

The produced benzene (Table I, column 6) is, on the contrary, of substantially higher purity than that obtained in the conditions of example 1.

EXAMPLE 3

The distillation is conducted under conditions identical to those described in example 1, except that:

(1) liquid water is injected at the level of the 65$^{th}$ plate (instead of steam), at a temperature of 25° C. and a flow rate of 4.9 g/h, (2) a reflux of non-aromatic organic phase equal to one tenth, i.e. 7.25 cc/h, of the withdrawn distillate amount, is injected.

The temperatures prevailing at both ends of the two columns are substantially identical to those mentioned in the preceding examples.

The non-aromatic distillate withdrawn at the top of the extraction column and the benzene withdrawn at the top of the column for the solvent regeneration have the compositions reported in Table II, respectively columns 4 and 5.

TABLE II

| CONSTITUENT | SOLVENT | CHARGE | DISTILLATE Example 3 | BENZENE Example 3 | BENZENE Example 4 |
|---|---|---|---|---|---|
| | | (% by weight) | | | |
| Hexane | — | 8.41 | 33.5 | <0.0010 | <0.0010 |
| Cyclohexane | — | 12.9 | 51.5 | 0.0426 | 0.0482 |
| Heptane | — | 3.45 | 13.6 | 0.0563 | 0.0625 |
| Methylcyclohexane | — | 0.13 | 0.44 | 0.0213 | 0.0231 |
| Benzene | <0.1 | 75.1 | 0.89 | >99.8 | >99.8 |
| Water | <0.1 | <0.05 | <0.05 | <0.05 | <0.05 |
| Dimethylformamide | >99.8 | — | 0.009 | <0.0010 | <0.0010 |

Water is completely vaporized without coming into contact with the solvent.

EXAMPLE 4 (comparative example)

The distillation is conducted under flow rate conditions identical to those described in example 3, but by injecting water as in example 1, i.e. on the 60$^{th}$ plate, said water being vaporized and brought to a temperature of 120° C. All water is discharged at the top.

The resulting non-aromatic distillate is, within experimental error, identical in amount and composition to the distillate of example 3 (Table II, column 4), except as concerns the dimethylformamide content which amounts to 0.026% by weight, i.e. about 3 times more than in the case of injection of liquid water.

The benzene discharged at the top of the column for the solvent regeneration (Table II, column 6), is of substantially lower purity than that obtained in the case of example 3, corresponding to an injection of liquid water.

EXAMPLE 5

In a distillation column of the Oldershaw type with 70 plates of the perforated type, having a 5 cm diameter, provided with a boiler and a head, there are injected respectively on the 30$^{th}$, 50$^{th}$ and 70$^{th}$ plates from the bottom:

(1) A benzenic cut whose composition is given in the second column of the Table, at a rate of 310 g/h and at a temperature of 55° C.

(2) Dimethylformamide at a rate of 1105 g/h and at a temperature of 65° C.

(3) Water preheated at 70° C., at a flow rate which depends on the temperature measured on the 55$^{th}$ and 60$^{th}$ plates. When the temperature at the 60$^{th}$ plate is higher than 80° C., the maximum water flow rate amounts to 27 g/h. When the temperature at the 55$^{th}$ plate is lower than 87° C., this flow rate is brought back to 20 g/h.

The distillate recovered from the head of the column, at a temperature of 68° C., is condensed and settled into two phases: a lower phase, consisting essentially of water which is recycled to the column at the precedingly defined level and an upper phase, whose composition is reported in the third column of the Table, consisting essentially of non-aromatic impurities of the benzenic cut, a portion of which, i.e. 115 g/h, is withdrawn and discharged from the system, the other portion being fed back to the column head as reflux, at a rate of 185 g/h.

At the bottom of the column, where the temperature is 129° C., there is withdrawn a mixture consisting essentially of benzene and dimethylformamide, which is fed to a second column of 40 plates operated according to a conventional distillation process, at reflux rate of 1.5.

From the top of said second column, there is withdrawn purified benzene whose analysis gives the results reported in the 4$^{th}$ column of the Table whereas, from the bottom, dimethylformamide is withdrawn and recycled, at a rate of 1105 g/h, to the first column.

| CONSTITUENTS | CHARGED BENZENIC FRACTION | ORGANIC DISTILLATE | FINAL BENZENE |
|---|---|---|---|
| Hexane | 11.2 | 32.6 | <0.001 |
| Heptane | 5.0 | 14.6 | <0.001 |
| Cyclohexane | 15.7 | 45.8 | <0.001 |
| Methylcyclohexane | 0.4 | 1.1 | 0.010 |
| Benzene | 67.7 | 5.9 | >99.98 |
| Dimethylformamide | 0. | <0.002 | <0.002 |

What we claim is:

1. In a process for separating at least one aromatic hydrocarbon selected from the group consisting of benzene and toluene, from a mixture containing the same together with at least one saturated paraffinic or cyclic hydrocarbon, in which said mixture is subjected to an extractive distillation in the presence of an extraction solvent, said extraction solvent being an aliphatic N-alkyl amide, said process comprising introducing the mixture of hydrocarbons to be separated to an intermediate point of a distillation zone, introducing said extraction solvent to a point of the distillation zone above said intermediate point, introducing H$_2$O into the distillation zone at a point of the distillation zone above the point of introduction of the extraction solvent, withdrawing from the bottom of said distillation zone the aromatic hydrocarbon and the extraction solvent, and withdrawing from the top of said distillation zone, a distillate substantially free of the extraction solvent and containing an azeotropic system of the saturated hydrocarbon and steam,
the improvement which comprises employing said H$_2$O in the form of liquid water, said liquid water being introduced into the distillation zone in such an amount and under such conditions as to be completely vaporized without substantially diluting said solvent, whereby said aromatic hydrocarbon is recovered in a higher purity as compared to the use of an equal amount of steam instead of liquid water.

2. A process according to claim 1, wherein the solvent is dimethylacetamide.

3. A process according to claim 1, wherein the solvent is dimethylacetamide.

4. A process according to claim 1, wherein water is used in an amount of at least 5% by weight and at most 50% by weight of the amount of saturated hydrocarbons.

5. A process according to claim 1, wherein water is used in an amount of at least 10% by weight and at most 35% by weight of the amount of saturated hydrocarbons.

6. A process according to claim 1, wherein the ratio by volume of the extraction solvent to the hydrocarbon mixture is from 0.4 to 15.

7. A process according to claim 1, wherein the ratio by volume of the extraction solvent to the hydrocarbon mixture is from 1 to 6.

8. A process according to claim 1, wherein the distillate is condensed, thereby forming two liquid phases, a saturated hydrocarbon phase and an aqueous phase, and at least a portion of the aqueous phase is recycled to the distillation zone, so as to form at least a portion of the liquid water introduced into said zone.

9. A process according to claim 1, wherein the saturated hydrocarbon has from 5 to 8 carbon atoms per molecule.

10. A process a-cording to claim 1, further comprising distilling the mixture of the aromatic hydrocarbon and the extraction solvent withdrawn from the bottom of the distillation zone so as to recover purified aromatic hydrocarbon.

11. A process according to claim 1, further comprising measuring the temperature at a point between the introduction of the solvent and the introduction of the liquid water into the distillation zone and adjusting the flow rate of the introduction of said liquid water in response to resultant measured temperature.

12. A process according to claim 11, wherein water is introduced at a flow rate which is reduced or nullified when the temperature decreases and is increased when the temperature increases.

13. A process according to claim 11, wherein two temperature measurements are made at two different levels located between the respective points of introduction of the solvent and of the water, and the water introduction is controlled in response to the temperature indicated by said measuring devices, the upper level temperature measurement being responsible for an increase in the water flow rate and the low temperature level measurement being responsible for a decrease in the water flow rate.

14. A process according to claim 11, wherein said process is performed in a plate distillation column, comprising a plurality of plates between the respective points of water and solvent introduction and in which the temperature measuring device is placed at a level at least equal to the level of the fourth plate above the solvent introduction point.

15. A process according to claim 11, wherein said process is performed in a plate column wherein 5 to 30 plates are provided between the point of water introduction and the point of solvent introduction.

* * * * *